United States Patent
De Beuckeleer (12) 
(10) Patent No.: US 6,395,485 B1
(45) Date of Patent: May 28, 2002

(54) METHODS AND KITS FOR IDENTIFYING ELITE EVENT GAT-ZM1 IN BIOLOGICAL SAMPLES

(75) Inventor: Marc De Beuckeleer, Ghent (BE)

(73) Assignee: Aventis CropScience N.V., Ghent (BE)

( * ) Notice: Subject to any disclaimer, the term of this patent is extended or adjusted under 35 U.S.C. 154(b) by 0 days.

(21) Appl. No.: 09/481,049

(22) Filed: Jan. 11, 2000

(51) Int. Cl.⁷ ............... C12Q 1/68; C12P 19/34; C07H 21/04
(52) U.S. Cl. .......... 435/6; 435/91.1; 435/91.2; 536/23.1; 536/24.3
(58) Field of Search .......... 435/6, 91.2, 91.1; 536/23.1, 24.3

(56) References Cited

U.S. PATENT DOCUMENTS 5,489,520 A    2/1996    Chambers et al.

FOREIGN PATENT DOCUMENTS

| | | |
|---|---|---|
| EP | EP 0 275 957 A | 7/1988 |
| EP | 0275 957 B1 | 3/1993 |
| WO | WO 95 22625 A | 8/1995 |
| WO | WO 98 30701 A | 7/1998 |
| WO | WO 01 31042 A | 3/2001 |

OTHER PUBLICATIONS

Accession No. E00019, Sep. 1997.*
Accession No. AR040951, Sep. 1998.*
Accession No. Q20951, Feb. 1992.*
Accession No. X20316, Dec. 1998.*
Engineering herbicide resistance in plants by expression of a detoxifying enzyme DeBlock et al., The EMBO Journal; vol. 6 No. 9 pp. 2513–2518, 1987.
Liu et al., "Efficient Isolation and Mapping of Arabidopsis Thaliana T–DNA Insert Junctions by Thermal Asymmetric Interlaced PCR", *The Plant Journal*, vol. 8, No. 3, 1995, pp. 457–463.
Thompson et al., "Characterization of the Herbicide–resistance Gene Bar from Streptomyces Hygroscopicus", *The EMBO Journal*, vol. 6, No. 9, 1987, pp. 2519–2523.

* cited by examiner

*Primary Examiner*—W. Gary Jones
*Assistant Examiner*—Jehanne Souaya
(74) *Attorney, Agent, or Firm*—Frommer Lawrence & Haug LLP (57) ABSTRACT

Tools are provided which allow rapid and unequivocal identification elite event GAT-ZM1 in biological samples.

15 Claims, 1 Drawing Sheet

SEQUENCE LISTING

<160> NUMBER OF SEQ ID NOS: 14

<210> SEQ ID NO 1
<211> LENGTH: 3983
<212> TYPE: DNA
<213> ORGANISM: Zea mays

<400> SEQUENCE: 1
tcgcgcgttt cggtgatgac ggtgaaaacc tctgacacat gcagctcccg gagacggtca    60

-continued

```
cagcttgtct gtaagcggat gccgggagca gacaagcccg tcaggcgcgc tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgcagggt    360 tttcccagtc acgacgttgt aaaacgacgg ccagtgccaa gcttgaattc gagctcggta    420
cccactggat tttggttta ggaattagaa attttattga tagaagtatt ttacaaatac    480
aaatacatac taagggtttc ttatatgctc aacacatgag cgaaaccccta aagaaccct    540 aattccctta tctgggaact actcacacat tattatagag agagatagat ttgtagagag    600
agactggtga tttcagcggc atgcctgcag gtcgactcag atctgggtaa ctggcctaac    660
tggccttgga ggagctggca actcaaaatc cctttgccaa aaaccaacat catgccatcc    720
accatgcttg tatccagctg cgcgcaatgt accccgggct gtgtatccca aagcctcatg    780
caacctaaca gatggatcgt ttggaaggcc tataacagca accacagact aaaaccttg    840 cgcctccata gacttaagca aatgtgtgta caatgtggat cctaggccca accttttgatg   900 cctatgtgac acgtaaacag tactctcaac tgtccaatcg taagcgttcc tagccttcca    960
gggcccagcg taagcaatac cagccacaac ccctcaacc tcagcaacca accaagggta   1020
tctatcttgc aacctctcta gatcatcaat ccactcttgt ggtgtttgtg gctctgtcct   1080
aaagttcact gtagacgtct caatgtaatg gttaacgata tcacaaaccg cggccatatc   1140
agctgctgta gctggcctaa tctcaactgg tctcctctcc ggagacatgt cgactctaga   1200
ggatccccgg gtaccctgtc ctctccaaat gaaatgaact tccttatata gaggaagggt   1260
cttgcgaagg atagtgggat tgtgcgtcat cccttacgtc agtggagata tcacatcaat   1320
ccacttgctt tgaagacgtg gttggaacgt ctcttttttc cacgatgctc ctcgtgggtg   1380
ggggtccatc tttgggacca ctgtcggcag aggcatcttc aacgatggcc tttccttttat   1440 cgcaatgatg gcatttgtag gagccacctt ccttttccac tatcttcaca ataaagtgac   1500
agatagctgg gcaatggaat ccgaggaggt ttccggatat tacccttttgt tgaaaagtct   1560 caattgccct ttggtcttct gagactgtat ctttgatatt tttggagtag acaagcgtgt   1620
cgtgctccac catgttgacg aagattttct tcttgtcatt gagtcgtaag agactctgta   1680
tgaactgttc gccagtcttt acggcgagtt ctgttaggtc ctctatttga atctttgact   1740
ccatgggaat tcgtaatcat ggtcatagct gtttcctgtg tgaaattgtt atccgctcac   1800
aattccacac aacatacgag ccggaagcat aaagtgtaaa gcctggggtg cctaatgagt   1860
gagctaactc acattaattg cgttgcgctc actgcccgct ttccagtcgg gaaacctgtc   1920
gtgccagctg cattaatgaa tcggccaacg cgcggggaga ggcggtttgc gtattgggcg   1980
ctcttccgct tcctcgctca ctgactcgct gcgctcggtc gttcggctgc ggcgagcggt   2040
atcagctcac tcaaaggcgg taatacggtt atccacagaa tcaggggata acgcaggaaa   2100
gaacatgtga gcaaaaggcc agcaaaaggc caggaaccgt aaaaaggccg cgttgctggc   2160 gttttccat aggctccgcc ccctgacga gcatcacaaa aatcgacgct caagtcagag   2220
gtggcgaaac ccgacaggac tataaagata ccaggcgttt ccccctggaa gctccctcgt   2280
gcgctctcct gttccgaccc tgccgcttac cggatacctg tccgcctttc tcccttcggg   2340
aagcgtggcg ctttctcata gctcacgctg taggtatctc agttcggtgt aggtcgttcg   2400
ctccaagctg ggctgtgtgc acgaaccccc cgttcagccc gaccgctgcg ccttatccgg   2460
```

```
taactatcgt cttgagtcca acccggtaag acacgactta tcgccactgg cagcagccac    2520
tggtaacagg attagcagag cgaggtatgt aggcggtgct acagagttct tgaagtggtg    2580
gcctaactac ggctacacta aaggacagt atttggtatc tgcgctctgc tgaagccagt     2640
```

```
taactatcgt cttgagtcca acccggtaag acacgactta tcgccactgg cagcagccac    2520
tggtaacagg attagcagag cgaggtatgt aggcggtgct acagagttct tgaagtggtg    2580
gcctaactac ggctacacta aaggacagt  atttggtatc tgcgctctgc tgaagccagt    2640
taccttcgga aaaagagttg gtagctcttg atccggcaaa caaaccaccg ctggtagcgg    2700
tggttttttt gtttgcaagc agcagattac gcgcagaaaa aaaggatctc aagaagatcc    2760
tttgatcttt tctacgggt  ctgacgctca gtggaacgaa aactcacgtt aagggatttt    2820
ggtcatgaga ttatcaaaaa ggatcttcac ctagatcctt ttaaattaaa aatgaagttt    2880
taaatcaatc taaagtatat atgagtaaac ttggtctgac agttaccaat gcttaatcag    2940
tgaggcacct atctcagcga tctgtctatt tcgttcatcc atagttgcct gactccccgt    3000
cgtgtagata actacgatac gggagggctt accatctggc cccagtgctg caatgatacc    3060
gcgagaccca cgctcaccgg ctccagattt atcagcaata aaccagccag ccggaagggc    3120
cgagcgcaga agtggtcctg caactttatc cgcctccatc cagtctatta attgttgccg    3180
ggaagctaga gtaagtagtt cgccagttaa tagtttcgc  aacgttgttg ccattgctac    3240
aggcatcgtg gtgtcacgct cgtcgtttgg tatggcttca ttcagctccg gttcccaacg    3300
atcaaggcga gttacatgat cccccatgtt gtgcaaaaaa gcggttagct ccttcggtcc    3360
tccgatcgtt gtcagaagta agttggccgc agtgttatca ctcatggtta tggcagcact    3420
gcataattct cttactgtca tgccatccgt aagatgcttt tctgtgactg gtgagtactc    3480
aaccaagtca ttctgagaat agtgtatgcg gcgaccgagt tgctcttgcc cggcgtcaat    3540
acgggataat accgcgccac atagcagaac tttaaaagtg ctcatcattg gaaaacgttc    3600 ttcgggcga  aaactctcaa ggatcttacc gctgttgaga tccagttcga tgtaacccac    3660
tcgtgcaccc aactgatctt cagcatcttt tactttcacc agcgtttctg ggtgagcaaa    3720
aacaggaagg caaaatgccg caaaaaaggg aataagggcg acacggaaat gttgaatact    3780
catactcttc ctttttcaat attattgaag catttatcag ggttattgtc tcatgagcgg    3840
atacatattt gaatgtattt agaaaaataa acaaataggg gttccgcgca catttccccg    3900
aaaagtgcca cctgacgtct aagaaaccat tattatcatg acattaacct ataaaaatag    3960
gcgtatcacg aggccctttc gtc                                            3983
```

<210> SEQ ID NO 2
<211> LENGTH: 16
<212> TYPE: DNA
<213> ORGANISM: Zea mays
<220> FEATURE:
<221> NAME/KEY: variation
<222> LOCATION: (1)..(16)
<223> OTHER INFORMATION: N stands for any nucleic acid
<220> FEATURE:
<221> NAME/KEY: variation
<222> LOCATION: (1)..(16)
<223> OTHER INFORMATION: S stands for G or C
<220> FEATURE:
<221> NAME/KEY: variation
<222> LOCATION: (1)..(16)
<223> OTHER INFORMATION: W stands forA or T/U

<400> SEQUENCE: 2
ngtcgaswga nawgaa                                                    16

<210> SEQ ID NO 3
<211> LENGTH: 22
<212> TYPE: DNA

```
<213> ORGANISM: Zea mays

<400> SEQUENCE: 3
tggatacaag catggtggat gg                                              22

<210> SEQ ID NO 4
<211> LENGTH: 21
<212> TYPE: DNA
<213> ORGANISM: Zea mays

<400> SEQUENCE: 4
aggcatgccg ctgaaatcac c                                               21

<210> SEQ ID NO 5
<211> LENGTH: 21
<212> TYPE: DNA
<213> ORGANISM: Zea mays

<400> SEQUENCE: 5
ggtttcgctc atgtgttgag c                                               21

<210> SEQ ID NO 6
<211> LENGTH: 1073
<212> TYPE: DNA
<213> ORGANISM: Zea mays

<400> SEQUENCE: 6
cgtcgagtga gatgaagtca cgacggggac tgactgcacc gtcgtctcag gtacgagggt     60
gacgtccagc aagcgtttcg cgagcvtgcc ggcgtcgtcc gtttgctcgg gattggcgtg    120
tcgcggggag acvgcvhcg tctttgtctc aaacvmgagg tcgatgcccg acgcgccccc    180
cgttggggcg ctggcgccgt cgactcgatc gacagccgac gaggcgctgc ctcctgcttg    240
accttggttg ccctgcctcc tcctccgtcg gcggggggaga ggacggggtg agctcgaatg    300
ttgttcttcc accacgcggg gaagacgtcg tcgattccac cctcatactc ttcctttttc    360
aatattattg aagcatttat cagggttatt gtctcatgag cggatacata tttgaatgta    420
tttagaaaaa taaacaaata ggggttccgc gcacatttcc ccgaaaagtg ccacctgacg    480
tctaagaaac cattattatc atgacattaa cctataaaaa taggcgtatc acgaggccct    540
ttcgtctcgc gcgtttcggt gatgacggtg aaaacctctg acacatgcag ctcccggaga    600
cggtcacagc ttgtctgtaa gcggatgccg ggagcagaca agcccgtcag ggcgcgtcag    660
cgggtgttgg cgggtgtcgg ggctggctta actatgcggc atcagagcag attgtactga    720
gagtgcacca tatgcggtgt gaaataccgc acagatgcgt aaggagaaaa taccgcatca    780
ggcgccattc gccattcagg ctgcgcaact gttgggaagg gcgatcggtg cgggcctctt    840
cgctattacg ccagctggcg aaaggggggat gtgctgcaag gcgattaagt tgggtaacgc    900
cagggttttc ccagtcacga cgttgtaaaa cgacggccag tgccaagctt gaattcgagc    960
tcggtaccca ctggattttg gttttaggaa ttagaaattt tattgataga agtatttac   1020
aaatacaaat acatactaag ggtttcttat atgctcaaca catgagcgaa acc          1073

<210> SEQ ID NO 7
<211> LENGTH: 22
<212> TYPE: DNA
<213> ORGANISM: Zea mays

<400> SEQUENCE: 7
ctcatggtta tggcagcact gc                                              22
```

<210> SEQ ID NO 8
<211> LENGTH: 23
<212> TYPE: DNA
<213> ORGANISM: Zea mays

<400> SEQUENCE: 8
ctgtcatgcc atccgtaaga tgc                                    23

<210> SEQ ID NO 9
<211> LENGTH: 20
<212> TYPE: DNA
<213> ORGANISM: Zea mays

<400> SEQUENCE: 9
tgctttgaag acgtggttgg                                        20

<210> SEQ ID NO 10
<211> LENGTH: 484
<212> TYPE: DNA
<213> ORGANISM: Zea mays

<400> SEQUENCE: 10
tgctttgaag acgtggttgg aacgtcttct ttttccacga tgctcctcgt gggtgggggt    60
ccatctttgg gaccactgtc ggcagaggca tcttcaacga tggcctttcc tttatcgcaa   120
tgatggcatt tgtaggagcc accttccttt tctactatct tcataataaa gtgacagata   180
gctgggcaat ggaatccgag gaggtttccg gatattaccc tttgttgaaa agtctcaatt   240
gccctttggt cttctgagac tgtatctttg atattttttgg agtagacaag cgtgtcgtgc   300
tccaccatgt tgacgaagat tttcttcttg tcattgagtc gttccgccat tgtcgctgtc   360
gcacggcggt ggaaggagta tcatgtcgta gctgccgtca agctccagat gggcagtctc   420
cagcaacctc tccggcccgg gacggtgctc cgtttcggga gtcttgagtt catctcactc   480
gacc                                                                484

<210> SEQ ID NO 11
<211> LENGTH: 22
<212> TYPE: DNA
<213> ORGANISM: Zea mays

<400> SEQUENCE: 11
gggtgagctc gaatgttgtt ct                                     22

<210> SEQ ID NO 12
<211> LENGTH: 22
<212> TYPE: DNA
<213> ORGANISM: Zea mays

<400> SEQUENCE: 12
tcttagacgt caggtggcac tt                                     22

<210> SEQ ID NO 13
<211> LENGTH: 22
<212> TYPE: DNA
<213> ORGANISM: Zea mays

<400> SEQUENCE: 13
agcgtcaagg atcattggtg tc                                     22

<210> SEQ ID NO 14

-continued

```
<211> LENGTH: 22
<212> TYPE: DNA
<213> ORGANISM: Zea mays

<400> SEQUENCE: 14
ggccaagttc agcataagct gt                                                 22
```

US 6,395,485 B1

METHODS AND KITS FOR IDENTIFYING ELITE EVENT GAT-ZM1 IN BIOLOGICAL SAMPLES

BACKGROUND OF THE INVENTION

The phenotypic expression of a transgene in a plant is determined both by the structure of the gene itself and by its location in the plant genome. At the same time the presence of the transgene (in a foreign DNA) at different locations in the genome will influence the overall phenotype of the plant in different ways. The agronomically or industrially successful introduction of a commercially interesting trait in a plant by genetic manipulation can be a lengthy procedure dependent on different factors. The actual transformation and regeneration of genetically transformed plants are only the first in a series of selection steps, which include extensive genetic characterization, breeding, and evaluation in field trials, eventually leading to the selection of an elite event.

The unequivocal identification of an elite event is becoming increasingly important in view of discussions on Novel Food/Feed, segregation of GMO and non-GMO products and the identification of proprietary material. Ideally, such identification method is both quick and simple, without the need for an extensive laboratory set-up. Furthermore, the method should provide results that allow unequivocal determination of the elite event without expert interpretation, but which hold up under expert scrutiny if necessary.

GAT-ZM1 was selected as an elite event in the development of corn resistant to the herbicide Liberty®, by transformation of corn with plasmid pUC/Ac comprising the pat gene encoding tolerance to phosphinothricin. It is commercially sold as. Liberty Link® maize, such as, for instance, Liberty Link® A6460LL sold by AgriGold/Akin Seed Company. The tools for use in simple and unequivocal methods for identification elite event GAT-ZM1 in biological samples are described herein.

SUMMARY OF THE INVENTION

The present invention relates to methods for identifying elite event GAT-ZM1 in biological samples, which methods are based on primers or probes which specifically recognize the 5' and/or 3' flanking sequence of GAT-ZM 1.

More specifically, the invention relates to a method comprising of amplifying a sequence of a nucleic acid present in biological samples, using a polymerase chain reaction with at least two primers, one of which recognizes the 5' or 3' flanking region of GAT-ZM1, the other which recognizes a sequence within the foreign DNA, to obtain a DNA fragment of between 100 and 350 bp. Preferably, the primers recognize a sequence within the 5' flanking region of GAT-ZM1, most preferably within the 5' flanking region of SEQ ID No. 6, and a sequence within the foreign DNA, respectively. Especially preferably, the primer recognizing the 5' flanking region comprises the nucleotide sequence of SEQ ID No 11 and the primer recognizing a sequence within the foreign DNA comprises the nucleotide sequence of SEQ ID No 12 described herein.

The present invention more specifically relates to a method for identifying elite event GAT-ZM1 in biological samples, which method comprises amplifying a sequence of a nucleic acid present in a biological sample, using a polymerase chain reaction with two primers having the nucleotide sequence of SEQ ID No 11 and SEQ ID No 12 respectively, to obtain a DNA fragment of between 180 and 220 bp, preferably of about 200 bp.

The present invention further relates to the specific flanking sequences of GAT-ZM1 described herein, which can be used to develop specific identification methods for GAT-ZM1 in biological samples. More particularly, the invention relates to the 5' and or 3' flanking regions of GAT-ZM1 which can be used for the development of specific primers and probes. The invention further relates to identification methods for the presence of GAT-ZM1 in biological samples based on the use of such specific primers or probes.

The invention further relates to kits for identifying elite event GAT-ZM1 in biological samples, said kits comprising at least one primer or probe which specifically recognizes the 5' or 3' flanking region of GAT-ZM1.

Preferably the kit of the invention comprises, in addition to a primer which specifically recognizes the 5' or 3' flanking region of GAT-ZM1, a second primer which specifically recognizes a sequence within the foreign DNA of GAT-ZM1, for use in a PCR identification protocol. Preferably, the kit of the invention comprises two specific primers, one of which recognizes a sequence within the 5' flanking region of GAT-ZM1, most preferably within the 5' flanking region of SEQ ID No. 6, and the other which recognizes a sequence within the foreign DNA. Especially preferably, the primer recognizing the 5' flanking region comprises the nucleotide sequence of SEQ ID No 11 and the primer recognizing the transgene comprises the nucleotide sequence of SEQ ID No 12 described herein.

The invention firther relates to a kit for identifying elite event GAT-ZM1 in biological samples, said kit comprising the PCR primers having the nucleotide sequence of SEQ ID No. 11 and SEQ ID No. 12 for use in the GAT-ZM1 PCR identification protocol described herein.

The invention also relates to a kit for identifying elite event GAT-ZM1 in biological samples, which kit comprises a specific probe having a sequence which corresponds (or is complementary to) a sequence having between 80% and 100% sequence identity with a specific region of GAT-ZM1 . Preferably the sequence of the probe corresponds to a specific region comprising part of the 5' or 3' flanking region of GAT-ZM1. Most preferably the specific probe has (or is complementary to) a sequence having between 80% and 100% sequence identity to the sequence between nucleotide 286 and 466 of SEQ ID No. 6.

The methods and kits encompassed by the present invention can be used for different purposes such as, but not limited to the following: to identify GAT-ZM1 in plants, plant material or in products such as, but not limited to food or feed products (fresh or processed) comprising or derived from plant material; additionally or alternatively, the methods and kits of the present invention can be used to identify transgenic plant material for purposes of segregation between transgenic and non-transgenic material; additionally or alternatively, the methods and kits of the present invention can be used to determine the quality (i.e. percentage pure material) of plant material comprising GAT-ZM1.

The invention further relates to the 5' and/or 3' flanking regions of GAT-ZM1 as well as to the specific primers and probes developed from the 5' and/or 3' flanking sequences of GAT-ZM1.

DETAILED DESCRIPTION

The incorporation of a recombinant DNA molecule in the plant genome typically results from transformation of a cell or tissue (or from another genetic manipulation). The particular site of incorporation is either due to "random" integration or is at a predetermined location (if a process of targeted integration is used).

The DNA introduced into the plant genome as a result of transformation of a plant cell or tissue with a recombinant DNA or "transforming DNA" is hereinafter referred to as "foreign DNA" comprising one or more "transgenes". Thus, foreign DNA may comprise both recombinant DNA as well as newly introduced, rearranged DNA of the plant. However, the term "plant DNA" in the context of the present invention will refer to DNA of the plant which is found in the same genetic locus in the corresponding wild-type plant. The foreign DNA can be characterized by the location and the configuration at the site of incorporation of the recombinant DNA molecule in the plant genome. The site in the plant genome where a recombinant DNA has been inserted is also referred to as the "insertion site" or "target site". Insertion of the recombinant DNA into the plant genome can be associated with a deletion of plant DNA, referred to as "target site deletion". A "flanking region" or "flanking sequence" as used herein refers to a sequence of at least 20 bp, preferably at least 50 bp, and up to 5000 bp of the plant genome which is located either immediately upstream of and contiguous with or immediately downstream of and contiguous with the foreign DNA. Transformation procedures leading to random integration of the foreign DNA will result in transformants with different flanking regions, which are characteristic and unique for each transformant. When the recombinant DNA is introduced into a plant through traditional crossing, its insertion site in the plant genome, or its flanking regions will generally not be changed. An "insertion region" as used herein refers to the region corresponding to the region of at least 40 bp, preferably at least 100 bp, and up to 10000 bp, encompassed by the sequence which comprises the upstream and/or the downstream flanking region of a foreign DNA in the plant genome. Taking into consideration minor differences due to mutations within a species, an insertion region will retain, upon crossing into a plant of the same species, at least 85%, preferably 90%, more preferably 95%, and most preferably 100% sequence identity with the sequence comprising the upstream and downstream flanking regions of the foreign DNA in the plant originally obtained from transformation.

An event is defined as a (artificial) genetic locus that, as a result of genetic manipulation, carries a transgene comprising at least one copy of a gene of interest. The typical allelic states of an event are the presence or absence of the foreign DNA. An event is characterized phenotypically by the expression of the transgene. At the genetic level, an event is part of the genetic makeup of a plant. At the molecular level, an event can be characterized by the restriction map (e.g. as determined by Southern blotting), by the upstream and/or downstream flanking sequences of the transgene, the location of molecular markers and/or the molecular configuration of the transgene. Usually transformation of a plant with a transforming DNA comprising at least one gene of interest leads to a multitude of events, each of which is unique.

An elite event, as used herein, is an event which is selected from a group of events, obtained by transformation with the same transforming DNA or by back-crossing with plants obtained by such transformation, based on the expression and stability of the transgene(s) and its compatibility with optimal agronomic characteristics of the plant comprising it. Thus the criteria for elite event selection are one or more, preferably two or more, advantageously all of the following:

a) That the presence of the foreign DNA does not compromise other desired characteristics of the plant, such as those relating to agronomic performance or commercial value;

b) That the event is characterized by a well defined molecular configuration which is stably inherited and for which appropriate tools for identity control can be developed;

c) That the gene(s) of interest show(s) a correct, appropriate and stable spatial and temporal phenotypic expression, both in heterozygous (or hemizygous) and homozygous condition of the event, at a commercially acceptable level in a range of environmental conditions in which the plants carrying the event are likely to be exposed in normal agronomic use.

It is preferred that the foreign DNA is associated with a position in the plant genome that allows easy introgression into desired commercial genetic backgrounds.

The status of an event as an elite event is confirmed by introgression of the elite event in different relevant genetic backgrounds and observing compliance with one, two or all of the criteria e.g. a), b) and c) above.

An "elite event" thus refers to a genetic locus comprising a foreign DNA, which answers to the above-described criteria. A plant, plant material or progeny such as seeds can comprise one or more elite events in its genome.

The tools developed to identify an elite event or the plant, plant material comprising an elite event, or products which comprise plant material comprising the elite event are based on the specific genomic characteristics of the elite event, such as, a specific restriction map of the genomic region comprising the foreign DNA, molecular markers or the sequence of the flanking region(s) of the foreign DNA.

Once one or both of the flanking regions of the foreign DNA have been sequenced, primers and probes can be developed which specifically recognize this (these) sequence(s) in the nucleic acid (DNA or RNA) of a sample by way of a molecular biological technique. For instance a PCR method can be developed to identify the elite event in biological samples (such as samples of plants, plant material or products comprising plant material). Such a PCR is based on at least two "specific primers" preferably one recognizing a sequence within the 5' or 3' flanking region of the elite event and the other recognizing a sequence within the foreign DNA. The primers preferably have a sequence of between 15 and 35 nucleotides which under optimized PCR conditions "specifically recognize" a sequence within the 5' or 3' flanking region of the elite event and the foreign DNA of the elite event respectively, so that a specific fragment ("integration fragment") is amplified from a nucleic acid sample comprising the elite event. This means that only the targeted integration fragment, and no other sequence in the plant genome or foreign DNA, is amplified under optimized PCR conditions.

Preferably, the integration fragment has a length of between 50 and 500 nucleotides, most preferably of between 100 and 350 nucleotides. Preferably the specific primers have a sequence which is between 80 and 100% identical to a sequence within the 5' or 3' flanking region of the elite event and the foreign DNA of the elite event, respectively, provided the mismatches still allow specific identification of the elite event with these primers under optimized PCR conditions. The range of allowable mismatches however, can easily be determined experimentally and are known to a person skilled in the art.

As the sequence of the primers and their relative location in the genome are unique for the elite event, amplification of the integration fragment will occur only in biological samples comprising (the nucleic acid of) the elite event. Preferably when performing a PCR to identify the presence of GAT-ZM1 in unknown samples, a control is included of a set of primers with which a fragment within a "housekeeping gene" of the plant species of the event can be amplified. Housekeeping genes are genes that are expressed in most cell types and which are concerned with basic metabolic activities common to all cells. Preferably, the fragment amplified from the housekeeping gene is a fragment which is larger than the amplified integration fragment. Depending on the samples to be analyzed, other controls can be included.

Standard PCR protocols are described in the art, such as in "PCR Applications Manual" (Roche Molecular Biochemicals, 2nd Edition, 1999). The optimal conditions for the PCR, including the sequence of the specific primers, is specified in a "PCR identification protocol" for each elite event. It is however understood that a number of parameters in the PCR identification protocol may need to be adjusted to specific laboratory conditions, and may be modified slightly to obtain similar results. For instance, use of a different method for preparation of DNA may require adjustment of, for instance, the amount of primers, polymerase and annealing conditions used. Similarly, the selection of other primers may dictate other optimal conditions for the PCR identification protocol. These adjustments will however be apparent to a person skilled in the art, and are furthermore detailed in current PCR application manuals such as the one cited above.

Alternatively, specific primers can be used to amplify an integration fragment that can be used as a "specific probe" for identifying GAT-ZM1 in biological samples. Contacting nucleic acid of a biological sample, with the probe, under conditions which allow hybridization of the probe with its corresponding fragment in the nucleic acid, results in the formation of a nucleic acid/probe hybrid. The formation of this hybrid can be detected (e.g. labeling of the nucleic acid or probe), whereby the formation of this hybrid indicates the presence of GAT-ZM1. Such identification methods based on hybridization with a specific probe (either on a solid phase carrier or in solution) have been described in the art. The specific probe is preferably a sequence which, under optimized conditions, hybridizes specifically to a region within the 5' or 3' flanking region of the elite event and preferably also comprising part of the foreign DNA contiguous therewith (hereinafter referred to as "specific region"). Preferably, the specific probe comprises a sequence of between 50 and 500 bp, preferably of 100 to 350 bp which is at least 80%, preferably between 80 and 85%, more preferably between 85 and 90%, especially preferably between 90 and 95%, most preferably between 95% and 100% identical (or complementary) to the nucleotide sequence of a specific region. Preferably, the specific probe will comprise a sequence of about 15 to about 100 contiguous nucleotides identical (or complementary) to a specific region of the elite event.

A "kit" as used herein refers to a set of reagents for the purpose of performing the method of the invention, more particularly, the identification of the elite event GAT-ZM1 in biological samples. More particularly, a preferred embodiment of the kit of the invention comprises at least one or two specific primers, as described above. Optionally, the kit can further comprise any other reagent described herein in the PCR identification protocol. Alternatively, according to another embodiment of this invention, the kit can comprise a specific probe, as described above, which specifically hybridizes with a specific region in the DNA of GAT-ZM1 in biological samples, to identify the presence of GAT-ZM1 nucleic acid therein. Optionally, the kit can further comprise any other reagent (such as but not limited to hybridizing buffer, label) for identification of GAT-ZM1 in biological samples, using the specific probe.

The kit of the invention can be used, and its components can be specifically adjusted, for purposes of quality control (e.g., purity of seed lots), detection of the elite event in plant material or material comprising or derived from plant material, such as but not limited to food or feed products.

As used herein, "sequence identity" with regard to nucleotide sequences (DNA or RNA), refers to the number of positions with identical nucleotides divided by the number of nucleotides in the shorter of the two sequences. The alignment of the two nucleotide sequences is performed by the Wilbur and Lipmann algorithm (Wilbur and Lipmann, 1983) using a window-size of 20 nucleotides, a word length of 4 nucleotides, and a gap penalty of 4. Computer-assisted analysis and interpretation of sequence data, including sequence alignment as described above, can, e.g., be conveniently performed using the programs of the IntelligeneticsTM Suite (Intelligenetics Inc., CA) or the sequence analysis software package of the Genetics Computer Group (GCG, University of Wisconsin Biotechnology center). Sequences are indicated as "essentially similar" when such sequences have a sequence identity of at least about 75%, particularly at least about 80%, more particularly at least about 85%, quite particularly about 90%, especially about 95%, more especially about 100%. It is clear than when RNA sequences are said to be essentially similar or have a certain degree of sequence identity with DNA sequences, thymidine (T) in the DNA sequence is considered equal to uracil (U) in the RNA sequence. "Complementary to" as used herein refers to the complementarity between the A and T (U), and G and C nucleotides in nucleotide sequences.

The term "primer" as used herein encompasses any nucleic acid that is capable of priming the synthesis of a nascent nucleic acid in a template-dependent process, such as PCR. Typically, primers are oligonucleotides from 10 to 30 basepairs, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a nucleic acid sequence in the elite event under the conditions set forth in the method (such as the conditions of the PCR identification protocol), whereby the specificity is determined by the presence of positive and negative controls.

The term "hybridizing" as used herein when referring to specific probes, refers to the fact that the probe binds to a specific region in the nucleic acid sequence of the elite event under standard stringency conditions. Standard stringency conditions as used herein refers to the condition for hybridization described herein or to the conventional hybridizing conditions as described by Sambrook et al. (1989) (Molecular Cloning: A Laboratory Manual, Second Edition, Cold Spring Harbour Laboratory Press, NY) which for instance can comprise the following steps: 1) immobilizing plant genomic DNA fragments on a filter, 2) prehybridizing the filter for 1 to 2 hours at 42° C. in 50% formamide, 5×SSPE, 2×Denhardt's reagent and 0.1% SDS, or for 1 to 2 hours at 68° C. in 6×SSC, 2×Denhardt's reagent and 0.1% SDS, 3) adding the hybridization probe which has been labeled, 4) incubating for 16 to 24 hours, 5) washing the filter for 20 min. at room temperature in 1×SSC, 0.1% SDS, 6) washing the filter three times for 20 min. each at 68° C. in 0.2×SSC, 0.1% SDS, and 7) exposing the filter for 24 to 48 hours to X-ray film at −70° C. with an intensifying screen.

As used in herein, a biological sample is a sample of a plant, plant material or products comprising plant material. The term "plant" is intended to encompass corn (Zea mays) plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts. "Plant material", as used herein refers to material which is obtained or derived from a plant. Products comprising plant material relate to food, feed or other products which are produced using plant material or can be contaminated by plant material. It is understood that, in the context of the present invention, such biological samples are tested for the presence of nucleic acids specific for GAT-ZM1, implying the presence of nucleic acids in the samples. Thus, the methods referred to herein for identifying elite event GAT-ZM1 in biological samples, relate to the identification in biological samples of nucleic acids which comprise the elite event.

As used herein "comprising" is to be interpreted as specifying the presence of the stated features, integers, steps, reagents or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA sequence which is functionally or structurally defined, may comprise additional DNA sequences, etc.

The following examples describe the development of tools for the identification of elite event GAT-ZM1 in biological samples.

Unless otherwise stated, all recombinant DNA techniques are carried out according to standard protocols as described in Sambrook et al. (1989) *Molecular Cloning: A Laboratory Manual,* Second Edition, Cold Spring Harbour Laboratory Press, NY and in Volumes 1 and 2 of Ausubel et al. (1994) *Current Protocols in Molecular Biology,* Current Protocols, USA. Standard materials and methods for plant molecular work are described in Plant Molecular Biology Labfax (1993) by R. D. D. Croy published by BIOS Scientific Publications Ltd (UK) and Blackwell Scientific Publications, UK.

In the description and examples, reference is made to the following sequences:

| | |
|---|---|
| SEQ ID No. 1: | sequence of the genetic elements of vector pUC/Ac |
| SEQ ID No. 2: | primer MDB286 |
| SEQ ID No. 3: | primer MDB391 |
| SEQ ID No. 4: | primer MDB411 |
| SEQ ID No. 5: | primer MDB420 |
| SEQ ID No. 6: | nucleotide sequence comprising a 5' flanking region of GAT-ZM1 |
| SEQ ID No. 7: | primer MDB439 |
| SEQ ID No. 8: | primer VDS44 |
| SEQ ID No. 9: | primer MDB522 |
| SEQ ID No. 10: | nucleotide sequence comprising a 3' flanking region of GAT-ZM1 |
| SEQ ID No. 11: | primer COR17 |
| SEQ ID No. 12: | primer COR18 |
| SEQ ID No. 13: | primer COR15 |
| SEQ ID No. 14: | primer COR16 |

BRIEF DESCRIPTION OF THE DRAWING

The following Examples, not intended to limit the invention to specific embodiments described, may be understood in conjunction with the accompanying Figure, incorporated herein by reference, in which.

EXAMPLES

1. Identification of the Flanking Regions of Elite Event GAT-ZM1

Herbicide-resistant corn was developed by transformation of corn with the pUC/Ac vector comprising the coding sequence of a pat gene encoding the enzyme phosphinothricin-acetyl-transferase, under the control of the constitutive 35S promoter from Cauliflower Mosaic virus. A detailed description of the genetic elements of pUC/Ac is provided in Table 1. The nucleotide sequence of the genetic elements of pUC/Ac is provided in SEQ ID No. 1.

TABLE genetic elements of vector pUC/Ac

| Nucleotide no. | Genetic element |
|---|---|
| 412–618 | 35S terminator from Cauliflower Mosaic Virus from the vector pDH51(Pietrzak M. et al., Nucleic Acids Res. 14, (1986), pp. 5857–5868) |
| 619–636 | Synthetic polylinker sequences |
| 637–1188 | Synthetic pat gene (amino acid sequence from *Streptomyces viridochromogenes*) (Strauch et al. (1993) European patent 275957 B1) |
| 1189–1216 | Synthetic polylinker sequences |
| 1217–1746 | 35S promoter from Cauliflower Mosaic Virus from the vector pDH51(Pietrzak M. et al., Nucleic Acids Res. 14, (1986), pp. 5857–5868) |
| 1747–411 | Sequence of the vector pUC18, including the β-lactamase gene (pos. 2923–3783) and the origin of replication at pos. 2164. (Yanisch-Perron et al., (1985), Gene 33, pp. 103–119) |

Elite event GAT-ZM1 was selected based on an extensive selection procedure based on good expression and stability of the herbicide resistance gene and its compatibility with optimal agronomic characteristics.

The sequence of the regions flanking the foreign DNA in the GAT-ZM1 event was determined using the thermal asymmetric interlaced (TAIL-) PCR method described by Liu et al. (1995, The Plant Journal 8(3):457–463). This method utilizes three nested primers in successive reactions together with a shorter arbitrary degenerate primer so that the relative amplification efficiencies of specific and non-specific products can be thermally controlled. The specific primers were selected for annealing to the border of the foreign DNA and based on their annealing conditions. A small amount (5 µl) of unpurified secondary and tertiary PCR products were analyzed on a 1% agarose gel. The tertiary PCR product was used for preparative amplification, purified and sequenced on an automated sequencer using the DyeDeoxy Terminator cycle kit.

1.1. Right (5') Flanking Region

The primers used were:

|  | Sequence (5' → 3') | Position in pUC/Ac |
|---|---|---|
| Degenerate primer MDB286 | NgT.CgA.SWg.ANA.WgA.A (SEQ ID No. 2) | — |
| Primary TAIL MDB391 | Tgg.ATA.CAA.gCA.Tgg.Tgg.ATg.g (SEQ ID No. 3) | 715 ← 736 |
| Secondary TAIL MDB411 | Agg.CAT.gCC.gCT.gAA.ATC.ACC (SEQ ID NO. 4) | 606 ← 626 |
| Tertiary TAIL MDB420 | ggT.TTC.gCT.CAT.gTg.TTg.AgC (SEQ ID No. 5) | 507 ← 527 |

Whereby: N = A,C,T or g; S = C or g; W = A or T

The fragment amplified using MDB286-MDB420 was ca. 1100 bp, the complete sequence of which was determined (SEQ ID No. 6). The sequence between nucleotide 1 and 341 corresponds to plant DNA, while the sequence between nucleotide 342 and 1041 corresponds to T-DNA

2. Left (3') Flanking Region

The primers used were:

|  | Sequence (5' → 3') | Position in pUC/Ac |
|---|---|---|
| Degenerate primer MDB286 | NgT.CgA.SWg.ANA.WgA.A (SEQ ID No. 2) | — |
| Primary TAIL MDB439 | CTC.ATg.gTT.ATg.gCA.gCA.CTg.C (SEQ ID No. 7) | 3401–3422 |
| Secondary TAIL VDS44 | CTg.TCA.TgC.CAT.CCg.TAA.gAT.gC (SEQ ID NO. 8) | 3435–3457 |
| Tertiary TAIL MDB522 | TgC.TTT.gAA.gAC.gTg.gTT.gg (SEQ ID No. 9) | 1326–1345 |

Whereby: N = A,C,T or g; S = C or g; W = A or T

The fragment amplified using MDB286-MDB522 was ca. 450 bp, the complete sequence of which was determined (SEQ ID No. 10). The sequence between nucleotide 1 and 342 corresponds to T-DNA, while the sequence between nucleotide 343 and 484 corresponds to plant DNA.

2. Development of a Polymerase Chain Reaction Identification Protocol

2.1. Primers

Specific primers were developed which recognize sequences within the elite event. More particularly, a primer was developed which recognizes a sequence within the 5' flanking region of GAT-ZM1. A second primer was then selected within the sequence of the foreign DNA so that the primers span a sequence of about 200 bp. The following primers were found to give particularly clear and reproducible results in a PCR reaction on GAT-ZM1 DNA:

COR17: 5'-ggg.TgA.gCT.CgA.ATg.TTg.TTC.T-3' (SEQ ID 11)
(target: plant DNA)

COR18: 5'-TCT.TAg.ACg.TCA.ggT.ggC.ACT.T-3' (SEQ ID 12)
(target: T-DNA)

Primers targeting an endogenous sequence are preferably included in the PCR cocktail. These primers serve as an internal control in unknown samples and in the DNA positive control. A positive result with the endogenous primer-pair demonstrates that there is ample DNA of adequate quality in the genomic DNA preparation for a PCR product to be generated. The endogenous primers were selected to recognize a housekeeping gene in Zea mays:

COR15: 5'-AgC.gTC.AAg.gAT.CAT.Tgg.TgT.C-3' (SEQ ID 13)
(located in Zea Mays alcohol dehydrogenase 1 gene (X04050))

COR16: 5'-ggC.CAA.gTT.CAg.CAT.AAg.CTg.T-3' (SEQ ID 14)
(located in Zea Mays alcohol dehydrogenase 1 gene (X04050))

2.2. Amplified Fragments

The expected amplified fragments in the PCR reaction are:

For primer pair COR15-COR16: 513bp (endogenous control)

For primer pair COR17-COR18: 202bp (GAT-ZM1 elite Event)

2.3. Template DNA

Template DNA was prepared from a leaf punch according to Edwards et al. (Nucleic Acid Research, 19, p1349, 1991). When using DNA prepared with other methods, a test, run utilizing different amounts of template should be done. Usually 50 ng of genomic template DNA yields the best results.

2.4. Assigned Positive and Negative Controls

To avoid false positives or negatives, it was determined that the following positive and negative controls should be included in a PCR run:

Master Mix control (DNA negative control). This is a PCR in which no DNA is added to the reaction. When the expected result, no PCR products, is observed this indicates that the PCR cocktail was not contaminated with target DNA.

A DNA positive control (genomic DNA sample known to contain the transgenic sequences). Successful amplification of this positive control demonstrates that the PCR was run under conditions which allow for the amplification of target sequences.

A wildtype DNA control. This is a PCR in which the template DNA provided is genomic DNA prepared from a non-transgenic plant. When the expected result, no amplification of a transgene PCR product but amplification of the endogenous PCR product, is observed this indicates that there is no detectable transgene background amplification in a genomic DNA sample.

2.5. PCR Conditions

Optimal results were obtained under the following conditions:

the PCR mix for 25$\mu$l reactions contains:
2.5 $\mu$l template DNA
2.5 $\mu$l 10×Amplification Buffer (supplied with Taq polymerase)
0.5 $\mu$l 10 mM dNTP's
0.5 $\mu$l COR17 (10 pmoles/$\mu$l)
0.5 $\mu$l COR18 (10 pmoles/$\mu$l)
0.25 $\mu$l COR15 (10 pmoles/$\mu$l)
0.25 $\mu$l COR16 (10 pmoles/$\mu$l)
0.1 $\mu$l Taq DNA polymerase (5 units/$\mu$l)
water up to 25 $\mu$l the thermocycling profile to be followed for optimal results is the following:

| | 4 min. at 95° C. |
|---|---|
| Followed by: | 1 min. at 95° C. |
| | 1 min. at 57° C. |

-continued

| | |
|---|---|
| | 2 min. at 72° C. |
| | For 5 cycles |
| Followed by: | 30 sec. at 92° C. |
| | 30 sec. at 57° C. |
| | 1 min. at 72° C. |
| | For 25 cycles |
| Followed by: | 5 minutes at 72° C. |

2.6. Agarose Gel Analysis

To optimally visualize the results of the PCR it was determined that between 10 and 20 μl of the PCR samples should be applied on a 1.5% agarose gel (Tris-borate buffer) with an appropriate molecular weight marker (e.g. 100 bp ladder PHARMACIA).

2.7. Validation of the Results

It was determined that data from transgenic plant DNA samples within a single PCR run and a single PCR cocktail should not be acceptable unless 1) the DNA positive control shows the expected PCR products (transgenic and endogenous fragments), 2) the DNA negative control is negative for PCR amplification (no fragments) and 3) the wild-type DNA control shows the expected result (endogenous fragment amplification).

When following the PCR Identification Protocol for GAT-ZM1 as described above, lanes showing visible amounts of the transgenic and endogenous PCR products of the expected sizes, indicate that the corresponding plant from which the genomic template DNA was prepared, has inherited the GAT-ZM1 elite event. Lanes not showing visible amounts of either of the transgenic PCR products and showing visible amounts of the endogenous PCR product, indicate that the corresponding plant from which the genomic template DNA was prepared, does not comprise the elite event. Lanes not showing visible amounts of the endogenous and transgenic PCR products, indicate that the quality and/or quantity of the genomic DNA didn't allow for a PCR product to be generated. These plants cannot be scored. The genomic DNA preparation should be repeated and a new PCR run, with the appropriate controls, has to be performed.

2.8. Use of Discriminating PCR Protocol to Identify GAT-ZM1

Before attempting to screen unknowns, a test run, with all appropriate controls, has to be performed. The developed protocol might require optimization for components that may differ between labs (template DNA preparation, Taq DNA polymerase, quality of the primers, dNTP's, thermocyler, etc.).

Amplification of the endogenous sequence plays a key role in the protocol. One has to attain PCR and thermocycling conditions that amplify equimolar quantities of both the endogenous and transgenic sequence in a known transgenic genomic DNA template. Whenever the targeted endogenous fragment is not amplified or whenever the targeted sequences are not amplified with the same ethidium bromide staining intensities, as judged by agarose gel electrophoresis, optimization of the PCR conditions may be required.

Zea mays leaf material from a number of plants, some of which comprising GAT-ZM1 were tested according to the above-described protocol. Samples from elite event GAT-ZM1 and from Zea mays wild-type were taken as positive and negative controls, respectively.

Figure 1:
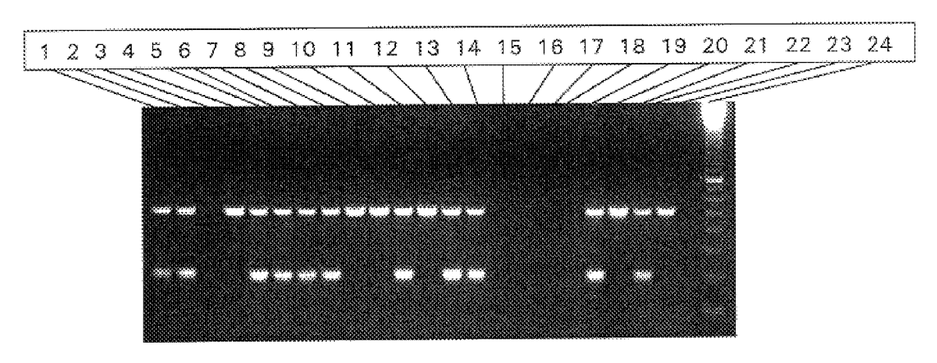
FIG. 1: Scoring of unknowns using the PCR Identification protocol developed for GAT-ZM1. Loading sequence of the gel: Unknowns: lanes 1, 2, 5, 6, 8, 11, 13, 14, DNA samples from corn plants comprising the transgenic event GAT-ZM1; lanes 4, 9, 10, 12, DNA samples from a corn plants not comprising elite event GAT-ZM1; lane 3, PCR failure. Control lanes: lanes 19, 21, control DNA samples from corn plants comprising elite event GAT-ZM1; lanes 20, 22, control DNA samples from wild-type corn plants; lane 23, no template control; lane 24, molecular weight marker.

FIG. 1 illustrates the result obtained with the elite event PCR identification protocol for GAT-ZM1 on a number of corn plant samples (lanes 1 to 14). The samples in lanes 1, 2, 5, 6, 7, 8, 11, 13, and 14 were found to contain the elite event as the 202 bp band is detected, while the samples in lanes 4, 9, 10, and 12 do not comprise GAT-ZM1. Lane 3 indicates a PCR failure, as the control band is not detected. Lanes 19 and 20 represent GAT-ZM1 positive control samples, lanes 20 and 22 represent non-transgenic Zea mays controls; lane 23 represents the negative control (water) sample, and lane 24 the Molecular Weight Marker (100 bp).

3. Use of a Specific Integration Fragment as a Probe for Detection of Material Comprising GAT-ZM1

A specific integration fragment of GAT-ZM1 is obtained by PCR amplification using specific primers COR17 (SEQ ID No. 11) and COR18 (SEQ ID No. 12) or by chemical synthesis and is labeled. This integration fragment is used as a specific probe for the detection of GAT-ZM1 in biological samples. Nucleic acid is extracted from the samples according to standard procedures. This nucleic acid is then contacted with the specific probe under hybridization conditions which are optimized to allow formation of a hybrid. The formation of the hybrid is then detected to indicate the presence of GAT-ZM1 nucleic acid in the sample. Optionally, the nucleic acid in the samples is amplified using the specific primers prior to contact with the specific probe. Alternatively, the nucleic acid is labeled prior to contact with the specific probe instead of the integration fragment. Optionally, the specific probe is attached to a solid carrier (such as, but not limited to a filter, strip or beads), prior to contact with the samples.

The above description of the invention is intended to be illustrative and not limiting. Various changes or modifications in the embodiments described may occur to those skilled in the art. These can be made without departing from the spirit or scope of the invention.

What is claimed is:

1. A method for identifying elite event GAT-ZM1 in biological samples, which method comprises detecting a GAT-ZM1 specific region with a specific primer or probe which specifically recognizes a sequence within the 5' flanking region in SEQ ID NO: 6 or the 3' flanking region in SEQ ID NO: 10 of GAT-ZM1.

2. The method of claim 1, said method comprising amplifying a DNA fragment of between 100 and 350 bp from a nucleic acid present in said biological samples using a polymerase chain reaction with at least two primers, the first of which recognizes the 5' flanking region in SEQ ID NO: 6 or 3' flanking region in SEQ ID NO: 10 of GAT-ZM1, the second of which recognizes a sequence within the foreign DNA of GAT-ZM1.

3. The method of claim 2, wherein said first primer recognizes a sequence within the 5' flanking region of GAT-ZM1 and said second primer recognizes a sequence within the said foreign DNA.

4. The method of claim 3, wherein said first and second primers comprise the sequence of SEQ ID NO: 11 and SEQ ID NO: 12, respectively.

5. The method of claim 4, which method comprises amplifying a fragment of between 150 and 220 bp using the GAT-ZM1 PCR identification protocol.

6. The method of claim 5, which method comprises amplifying a fragment of about 202 bp, using the GAT-ZM1 PCR identification protocol.

7. A kit for identifying elite event GAT-ZM1 in biological samples which detects a GAT-ZM1 specific region, said kit comprising at least a first PCR primer, which recognizes a sequence within the 3' flanking region in SEQ ID NO: 10 or the 5' flanking region in SEQ ID NO: 6 of GAT-ZM1.

8. The kit of claim 7, which further comprises at least a second PCR primer which recognizes a sequence within the foreign DNA of GAT-ZM 1.

9. The kit of claim 7, wherein said first PCR primer recognizes a sequence within the 5' flanking region of SEQ ID No. 6.

10. The kit of claim 8, wherein said at least first and second PCR primers comprise the sequence of SEQ ID NO: 11 and SEQ ID NO: 12, respectively.

11. The method of claim 1, which method comprises hybridizing a nucleic acid from a biological sample with a specific probe for the GAT-ZM1 specific region.

12. The method of claim 11, wherein the sequence of said specific probe has at least 80% sequence identity with a sequence comprising SEQ ID NO: 6.

13. A kit for identifying elite event GAT-ZM1 in biological samples, said kit comprising a specific probe comprising a sequence which hybridizes with the 5' flanking sequence in SEQ ID NO: 6 of GAT-ZM1 and the sequence of the foreign DNA contiguous therewith.

14. A method for confirming seed purity, which method comprises detection of a GAT-ZM1 specific region with a specific primer or probe which specifically recognizes the 5' flanking region of SEQ ID NO: 6 or the 3' flanking region of SEQ ID NO: 10 of GAT-ZM1, in seed samples.

15. A method for screening seeds for the presence of GAT-ZM1, which method comprises detection of a GAT-ZM1 specific region with a specific primer or probe which specifically recognizes the 5' flanking region of SEQ ID NO: 6 or the 3' flanking region of SEQ ID NO: 10 of GAT-ZM1, in samples of seed lots.

* * * * *